United States Patent [19]

Hamacher

[11] Patent Number: 5,078,691
[45] Date of Patent: Jan. 7, 1992

[54] MULTIPLE-DOSE FLUID DELIVERY SYSTEM AND METHOD

[76] Inventor: Edward N. Hamacher, 706 W. 6th Ave., Apt. 13, Spokane, Wash. 99204

[21] Appl. No.: 487,594

[22] Filed: Mar. 1, 1990

[51] Int. Cl.[5] ............................................. A61M 5/00
[52] U.S. Cl. ......................................... 604/191; 604/89; 604/218; 604/248; 604/183
[58] Field of Search ............... 604/187, 191, 190, 218, 604/221, 226, 248, 89, 82, 186, 183; 128/763-765

[56] References Cited

U.S. PATENT DOCUMENTS

| 212,046 | 2/1879 | Palmer . | |
|---|---|---|---|
| 213,978 | 4/1879 | Dibble . | |
| 553,234 | 1/1896 | Finot | 604/191 X |
| 657,440 | 9/1900 | McCaw | 604/191 X |
| 708,224 | 9/1902 | Gundlach et al. | 604/191 X |
| 1,707,880 | 4/1929 | Sheets | 604/89 X |
| 1,831,668 | 11/1931 | Juhl | 604/248 X |
| 1,950,137 | 3/1934 | Dowe | 604/89 X |
| 3,052,240 | 9/1962 | Silver et al. | 604/89 |
| 3,157,481 | 11/1964 | Bujan | 604/190 X |
| 3,749,084 | 7/1973 | Cucchiara | 604/191 X |
| 3,872,864 | 3/1975 | Allen | 604/89 |
| 4,381,778 | 5/1983 | Kozam et al. | 604/191 |
| 4,543,094 | 9/1985 | Barnwell | 604/236 |
| 4,610,666 | 9/1986 | Pizzino | 604/191 |
| 4,655,747 | 4/1987 | Allen | 604/89 |
| 4,738,660 | 4/1988 | Lucas | 604/139 |
| 4,740,203 | 4/1988 | Hoshkins et al. | 604/191 |
| 4,795,441 | 1/1989 | Bhatt | 604/124 |

FOREIGN PATENT DOCUMENTS 737249  6/1966 Canada ............................... 604/191
1204215  7/1984 U.S.S.R. .

Primary Examiner—C. Fred Rosenbaum
Assistant Examiner—Mark O. Polutta
Attorney, Agent, or Firm—Michael J. Folise

[57] ABSTRACT

A multiple-dose reservoir syringe and manifold fluid delivery system are disclosed. The multiple-dose syringe has an inner cylindrical chamber which is selectively communicable with an outer annular fluid reservoir. The fluid can be withdrawn from the outer reservoir to the inner chamber for subsequent ejection therefrom. Means are provided for maintaining the sterility of the fluid stored in the outer reservoir.

8 Claims, 5 Drawing Sheets

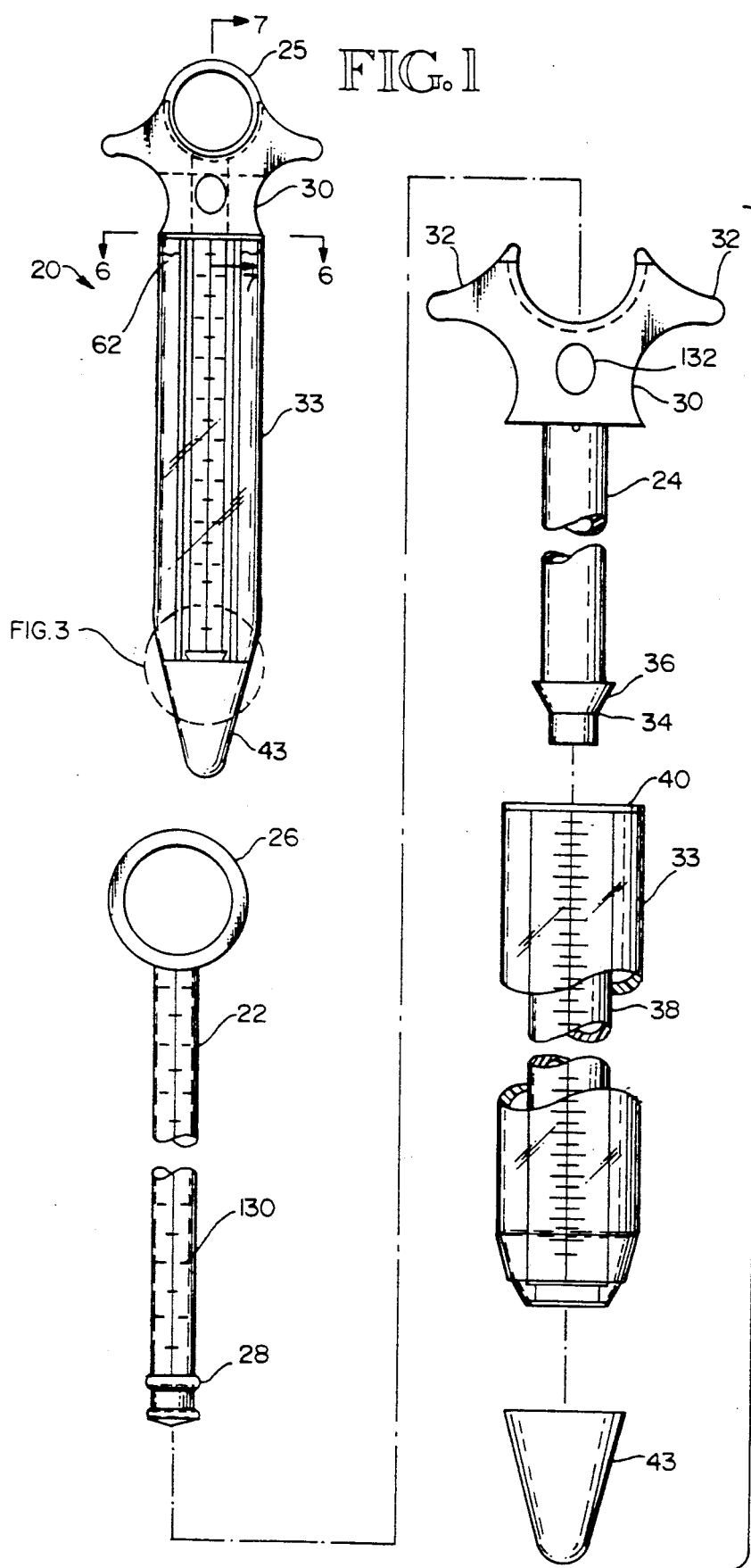

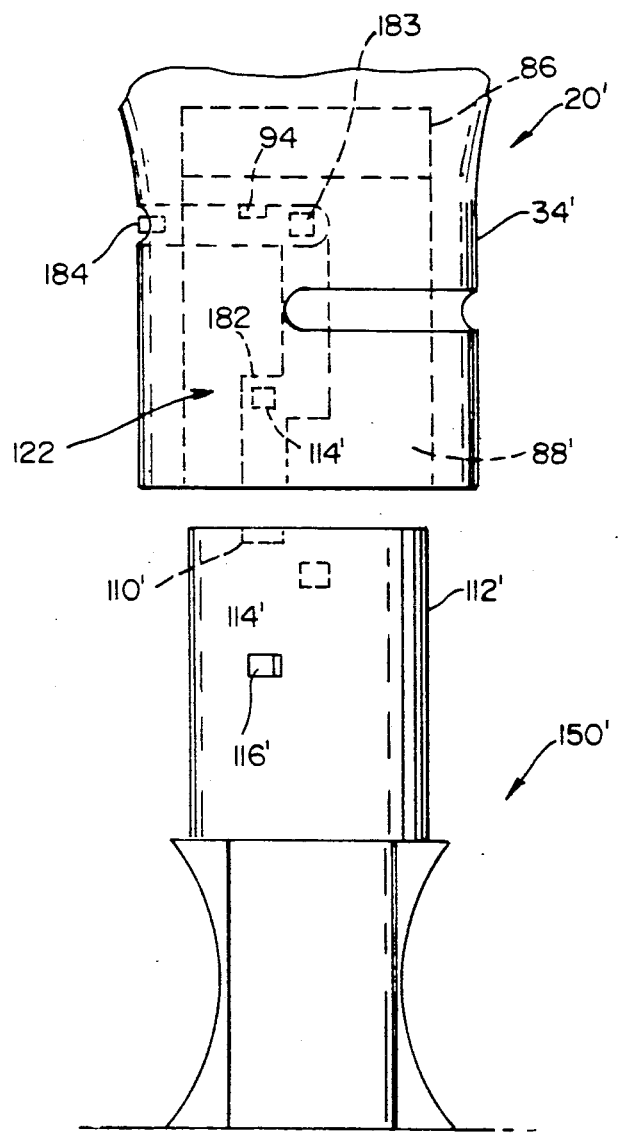

MULTIPLE-DOSE FLUID DELIVERY SYSTEM AND METHOD

TECHNICAL FIELD

The invention relates to apparatus and methods for injecting patients with multiple doses of medicaments. More specifically, the invention relates to methods and techniques for reducing the transmission of infectious diseases when medicating a patient.

BACKGROUND OF THE INVENTION

The recent and rapid growth in the transmission of infectious diseases has produced a heightened level of awareness in health care workers regarding such transmissions. In particular, the recent introduction of human immunodeficiency virus (HIV) into the general population has cause a great deal of concern among health care practitioners for their own safety, and for the safety of their patients. In addition, other highly contagious diseases, such as hepatitis B, have become the subject of stringent procedures in health care facilities to prevent the spread of such diseases among patients and health care practitioners.

Many of these safety procedures focus on the use of shields or other devices to prevent the transfer of bodily fluids from the patient to the health care practitioner. In addition, stringent safety procedures have been adopted for disposal of needles, catheters, etc., which come into contact with bodily fluids.

The direct injection of medicaments into patients is an area of potential direct contamination and potential cross-contamination between patients which has received little attention. Traditionally, patients are injected with medicine contained in a vial which is drawn into a conventional hypodermic syringe. The medicine vial is closed by a self-sealing membrane. Medicine is drawn into the syringe by piercing the vial membrane with the hypodermic needle. Different patients may be injected with fluid from the same vial. Although different patients are infected through different sterile hypodermic needles, every time the medicine vial seal is broken by a needle, airborne contaminants residing on the needle are introduced into the vial. Thus, the vial becomes a common source of contamination for all patients. In addition, in the event that any needle, prior to its introduction into the medicine vial, is contaminated by other contaminants, such as bodily fluids, the medicine vial can become a common source of contamination for transmission of various diseases.

One solution to the above cross-contamination problem is the pre-packaging of medicines within individual hypodermic syringes. U.S. Pat. Nos. 3,872,864, to Allen, Jr.; 213,978, to Dibble; 212,046, to Palmer; and Soviet Patent No. 1,204,215 all disclose hypodermic needles having their own fluid reservoirs. Nevertheless, each of the devices disclosed in these patents permits the entry of air containing microbial contaminants into its fluid reservoir chamber when the syringe portion of such device is charged from its fluid reservoir chamber. Furthermore, in each of these devices, the hypodermic needle is attached to the syringe in such a manner that the attachment point is exposed to possible contamination from the hands of a user. Thus, the problem of maintaining the medicine within these self-contained syringes in a sterile condition has not been fully resolved.

Thus, a need exists for a multiple-dose fluid delivery system which carries its own medicine for injection into a single patient and which maintains the sterility of the fluid throughout multiple doses.

A further need exists for a multiple-dose fluid delivery system which can medicate a patient with a variety of different medicines simultaneously while maintaining the sterility of each of the fluid medicaments.

SUMMARY OF THE INVENTION

It is therefore an object of the present invention to provide a multiple-dose fluid delivery system which provides a fluid reservoir for the delivery of medicinal fluid to a single patient and which maintains the sterility of such fluid throughout the injection of multiple doses.

It is also an object of the invention to provide a sterile fluid delivery system which can introduce a multiplicity of different medicaments into a patient at various times while maintaining the sterility of such fluids.

The invention achieves these and other objects and advantages, which will become apparent from the description which follows, by providing a multiple-dose fluid delivery system which has a first chamber for accepting a charge of fluid and a second chamber for storing fluid in a sterile manner. The chambers can be selectively communicated with one another for transfer of the fluid from the second chamber to the first chamber. A vent mechanism is provided which permits the entry of air into the second chamber while the first chamber is charged with fluid. The vent mechanism permits entry of air into the second chamber but excludes undesirable microorganisms and other contaminants therefrom.

In its preferred embodiment, the invention also includes a fluid-ejection valve which is selectively engageable with the first chamber to permit ejection of fluid therefrom. The fluid-ejection valve is constructed in such a manner so as to be engageable with a hypodermic needle or other external member in a sterile manner. Relative rotation of the hypodermic needle or other external member with respect to the first chamber establishes fluid communication therebetween. Counter-rotation of the hypodermic needle or other external member terminates the fluid communication and seals the first chamber from the external environment. In this manner, both the first and second chambers are isolated from external contaminants while the first chamber is charged with fluid and in the period between administration of subsequent injections.

In an alternate embodiment, a mechanism is provided for loosely retaining the hypodermic needle, or other external member, to the first or second chamber in such a manner that the fluid-ejection valve is not engaged, thus preventing accidental ejection of fluid from the first chamber.

A multiple medicine delivery device and system are also provided which permit the injection of a variety of different medicines to a patient in a sterile manner.

BRIEF DESCRIPTION OF THE DRAWINGS

FIG. 1 is a side elevational view of a multiple-dose reservoir syringe in accordance with the present invention.

FIG. 2 is an exploded, side elevational view of the multiple-dose reservoir syringe of FIG. 1.

FIG. 10 is an enlarged partial view of an alternate embodiment of the invention corresponding to the circled area in FIG. 9.

DETAILED DESCRIPTION OF THE INVENTION

Figure 3:
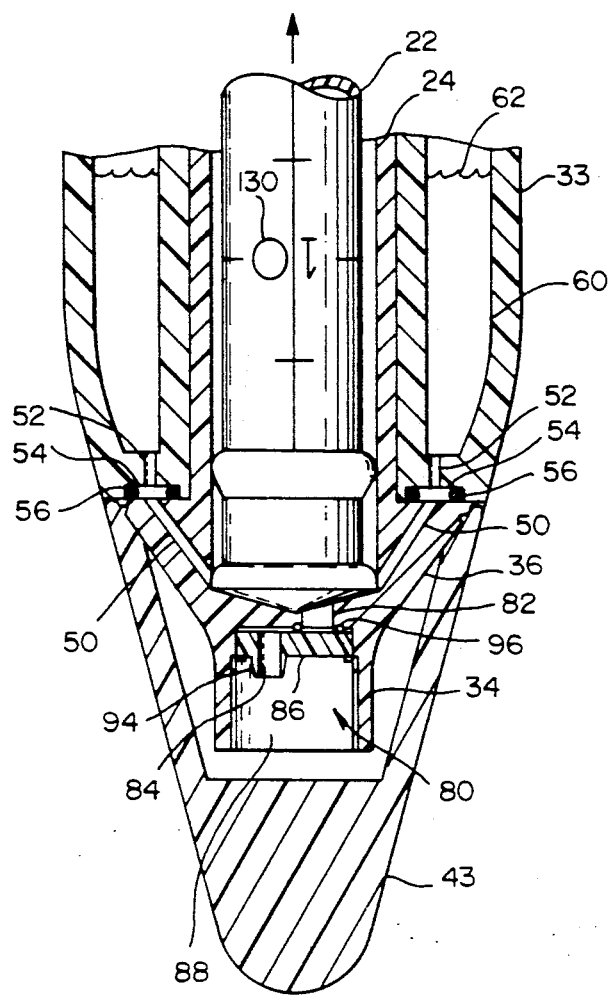
FIG. 3 is an enlarged sectional view of the circled area indicated in FIG. 1.

A multiple-dose reservoir syringe, in accordance with the principles of the invention, is generally indicated at reference numeral 20 in FIG. 1. As best seen in FIG. 2, the syringe has a plunger 22, an inner cylinder 24, and an outer annular cylinder 32. The syringe 20 and all of its constituent parts are preferably constructed from molded polypropylene, surgical-grade silicone, or the like.

The plunger 22 has a ring 26 at one and for grasping by a finger or the like. The other end of the plunger supports a conventional piston 28, which is sized for reciprocal motion within the inner cylinder 24. The inner cylinder 24 has an enlarged member 30 at its upper end, having tabs 32 thereon adapted to facilitate rotation of the inner cylinder 24 with respect to an outer cylinder 33 for a purpose which will be described hereinbelow. The inner cylinder 24 also has a lower end 34 having an enlarged diameter flange 36. The flange and enlarged member journal the inner cylinder 24 for rotation within the inner wall 38 of the outer cylinder 33, as best seen in FIGS. 3 and 2.

Figure 6:
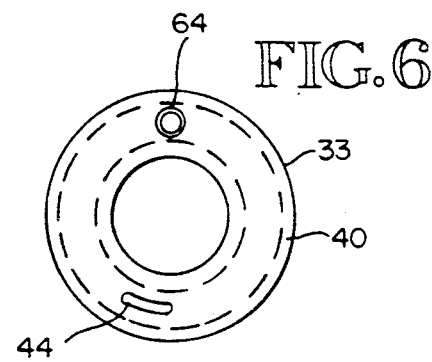
FIG. 6 is a sectional view, taken along line 6—6 of FIG. 1.
Figure 7:
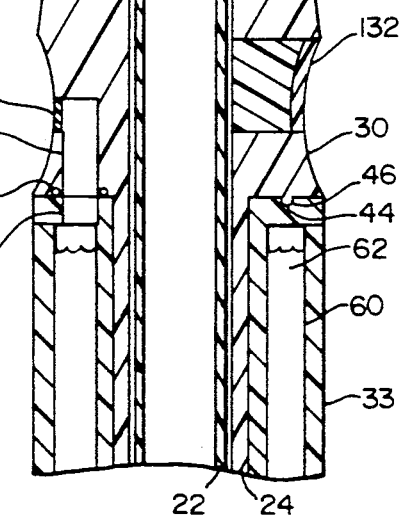
FIG. 7 is an enlarged sectional view taken along line 7—7 of FIG. 1.

The outer cylinder 33 has an upper surface 40, as best seen in FIG. 6, which has an arc-shaped depression 44 therein for the purpose of limiting the relative rotation of the inner cylinder 24 with respect to the outer cylinder 33. As best seen in FIG. 7, the enlarged member 30 of the inner cylinder 24 has a protrusion 46 sized to engage the depression 44. The depression 44 subtends an arc of approximately twenty degrees so that the relative rotation of the inner and outer cylinders is limited over this range.

As best seen in FIG. 3, the flange 36 of the inner cylinder 24 has two fluid introduction channels 50, which are selectively registrable with fluid channels 52 in the outer cylinder 33. Although two pairs of such registrable channels are shown, more or fewer may be provided. Seats 54 are provided in the outer cylinder 33 for O-ring seals 56. The seats and seals are positioned so as to prevent leakage at the junction of the channels 50 and 52 when the channels are in registration with one another.

As shown in FIG. 3, registration of the channels 50 and 52 provides a fluid pathway from a fluid reservoir 60 in the outer cylinder 26 to the interior cavity defined by the inner cylinder 24. Thus, when the channels 50 and 42 are in registration with one another, retraction of the plunger 22 causes fluid 62 in the fluid reservoir 60 to be drawn through the channels 50 and 52 into the inner cylinder 24 for subsequent ejection therefrom.

The outer cylinder 33 and enlarged member 30 of the inner cylinder 24 are provided with vent passages 64, 66, respectively, which permit the entry of air into the fluid reservoir 60 when the channels 50, 52 are aligned and when the plunger 22 is withdrawn. The vent passages prevent the formation of a vacuum when the plunger is withdrawn. The vent passages are located so as to be aligned only when the fluid channels 50, 52 are aligned.

The vent passage 66 on the enlarged member 30 is provided with a filter member 68 which permits the entry of air into the fluid reservoir 60 but which prevents the passage of bacteria or other undesirable contaminants into the fluid reservoir. A suitable microporous filter material is available from Millipore Corporation, Bedford, Massachusetts. This material has a porosity of approximately 0.2 micrometer to 0.45 micrometer. Those of ordinary skill in the art will appreciate that other materials may be satisfactorily substituted for the described microporous membrane, provided that the substituted material prevents the entry of undesirable bacteria and contaminants into the fluid reservoir 60. A seal, such as O-ring seal 70, is provided between the vent passages 64, 66 to prevent leakage of fluid from the junction therebetween.

One purpose of the invention is to permit the ejection of sterile fluid from inside the inner cylinder 24 to a patient in such a manner that the sterility of the fluid contained in the fluid 62 reservoir 60 is maintained in a sterile condition through a multiplicity of injections. To maintain a sterile ejection path for fluid from the inner cylinder 24, the lower end 34 of the inner cylinder 24 is provided with a fluid-ejection valve generally indicated at reference numeral 80 in FIG. 3. The ejection valve 80 includes a fluid-ejection channel 82 at the lower end of the inner cylinder 24. The fluid-ejection channel is displaced from the axis of the inner cylinder 24 so as to be registrable with a fluid-ejection aperture 84, defined by a rotatable disk 86.

The disk 86 is received for rotation within a recessed cavity 88 of the lower end 34. The aperture 84 is displaced from the center of rotation of the disk 86 so that rotation of the disk selectively aligns and misaligns the aperture 84 with the fluid-ejection channel 82. The disk also has a hollow projection 94 which surrounds and axially extends the aperture 84. A seal, such as O-ring seal 96, is provided between the disk 86 and the fluid-ejection channel 82.

Figure 5:
FIG. 5 is an enlarged, exploded, isometric view illustrating engagement of a hypodermic needle with an operative portion of a fluid-ejection valve of the invention.
Figure 4:
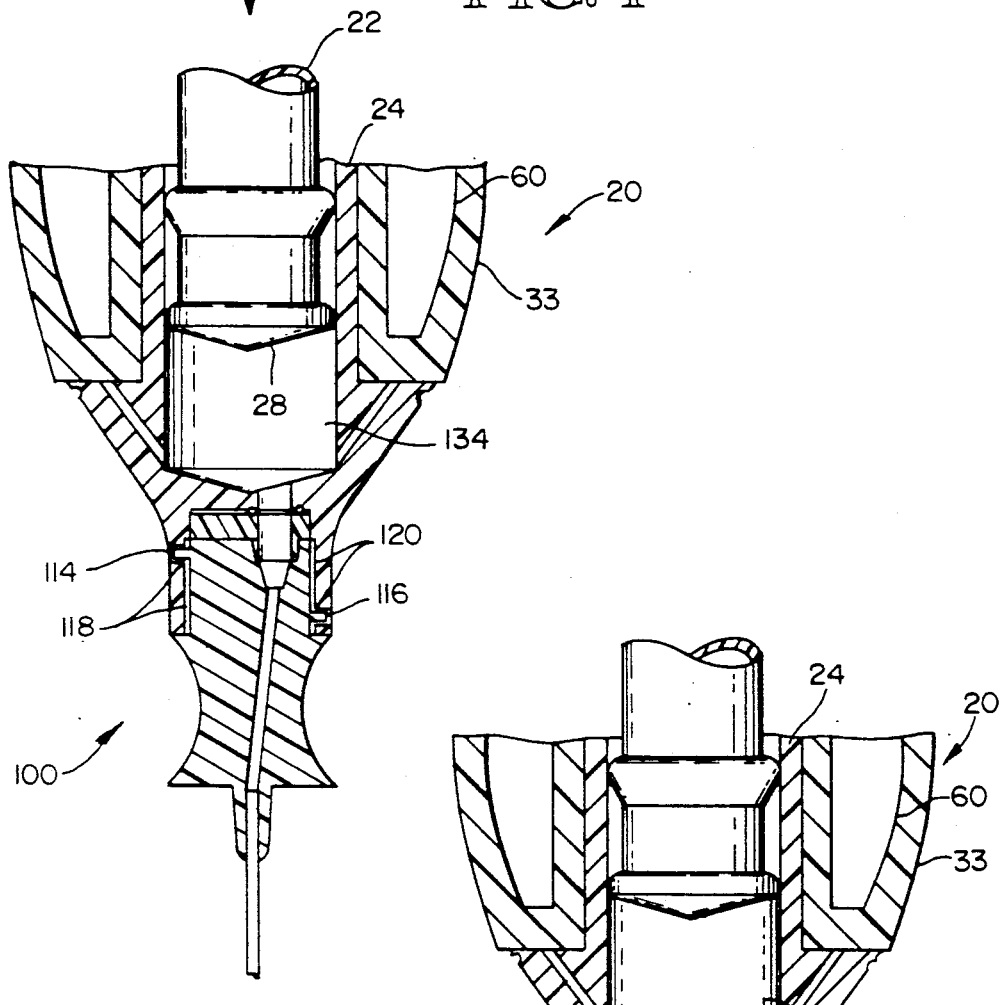
FIG. 4 is an enlarged sectional view, similar to FIG. 3, showing the invention in use with a hypodermic needle.
Figure 8:
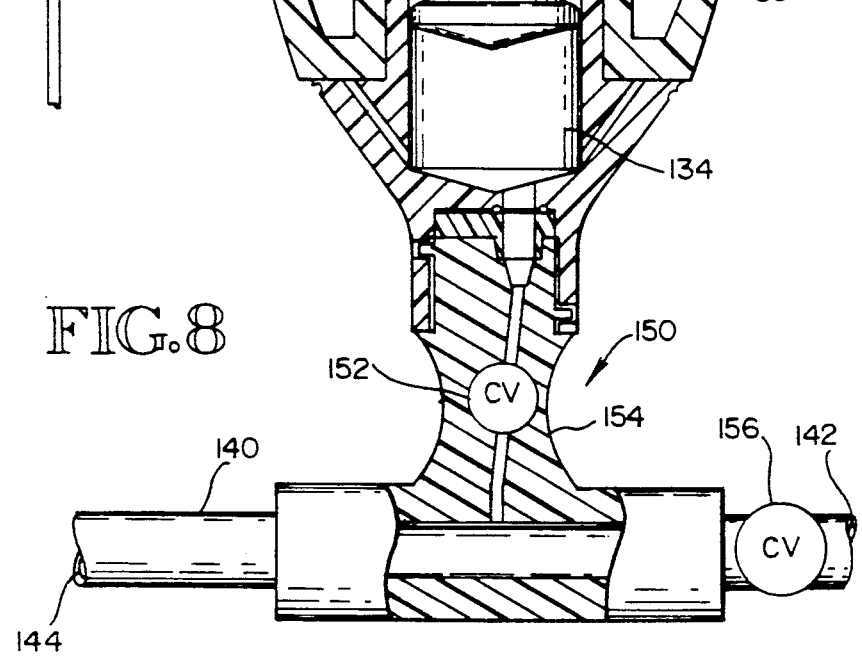
FIG. 8 is an enlarged sectional view showing the multiple-dose syringe of the invention in use with an external member.

As best seen in FIGS. 4, 5, and 8, an external member, such as hypodermic needle 100, defines an off-center aperture 110, which is engageable with the projection 94 on the rotatable disk 86. Thus, rotation of the external member is transferred to the disk as long as the aperture 110 is engaged with the projection 94. The rotatable disk 86 is well recessed within the cavity 88 so as to discourage contact between any portion of the disk 86 and the external environment, including the hands of the user. Therefore, as long as the aperture 110 remains uncontaminated, the entire fluid-ejection path remains sterile.

As best seen in FIGS. 4 and 5, the external member, such as hypodermic needle 100, is provided with a reduced diameter portion 112 having radially extending upper ears 114 and lower ears 116 which mate with corresponding grooves 118, 120 in the lower end 34 of the inner cylinder 24. The ears and grooves form the male and female portions, respectively, of a bayonet mechanism for locking the external member, such as hypodermic needle 100, into mating engagement with the rotating disk 86. As shown in FIGS. 3 and 4, the external member can only be inserted into a mating position with the rotating disk 86 when the fluid-ejection aperture 84 is in the misaligned position with the fluid-ejection channel 82, as shown in FIG. 3. Upon rotation of the external member and the disk 86 to the fluid-ejection position shown in FIG. 4, the external member 100 is in a locked position, during which it cannot be disengaged from the recessed cavity 88.

The lower end 34 of the syringe 20 may be protected by a cap 48 during transit of the syringe.

OPERATION OF THE INVENTION

In a first example, operation of the invention for direct injection of fluid into a patient through a hypodermic needle is described. Before drawing fluid from the fluid reservoir 60 into the inner cylinder 24, the fluid channels 50 and 52 are aligned, as shown in FIG. 3, by rotating the inner and outer cylinders 24, 33 with respect to one another. In this aligned position, the vent passages 64 and 66 are also in alignment, as shown in FIG. 7. The rotating disk 86 is preferably in the misaligned position, as shown in FIG. 3, to prevent entry of air into the inner cylinder 24. The external member, for example, hypodermic needle 100, may or may not be engaged in the recessed cavity 88, but is preferably engaged and not rotated into the fluid delivery position shown in FIG. 4.

The plunger 26 is then withdrawn to a position corresponding to the desired volume of fluid to be ejected. Calibration markings 130 may be viewed through an optical window 132, shown in FIG. 7.

After the desired volume of fluid has been drawn into the inner cylinder 24, the outer cylinder 33 and inner cylinder 24 are rotated so that the fluid channels 50 and 52 are misaligned, as shown in FIG. 4. The external member, such as hypodermic needle 100, is then rotated to the fluid delivery position, shown in FIG. 4, for subsequent depression of the plunger 22 for ejection of the fluid charge 134.

Subsequent injections of medicine from the multiple-dose reservoir syringe 20' can be made by repeating the above procedure. The hypodermic needle 100 should be changed between the drawing of each fluid charge 134 so that a sterile needle is always used.

FIG. 8 illustrates use of the multiple-dose reservoir syringe 20' in an intravenous line 140. The upstream end of the line may be connected, for example, to a conventional intravenous drip-bag, while the downstream end 144 may be connected to a conventional intravenous needle in the patient's arm. In this example, the external member 150 is a T-connector having the same male-type bayonet connector as does the hypodermic needle 100 of FIGS. 4 and 5. However, a first check valve 152 is provided in a root portion 154 of the T-connector to prevent backflow of fluid from the intravenous drip-bag into the inner cylinder 24. A second check valve is provided at the upstream end 142 of the intravenous line 140 to prevent backflow of the fluid charge 134 from the multiple-dose reservoir syringe 20 to the intravenous drip-bag. With the apparatus shown in FIG. 8, multiple doses of fluid at selected intervals can be delivered to a patient in conjunction with a conventional intravenous drip system. This system, as shown in FIG. 8, advantageously eliminates the repeated puncturing of a membrane on the IV line, as is required by conventional hypodermic injection. Thus, a major source of contamination and possible infection is eliminated.

Figure 9:
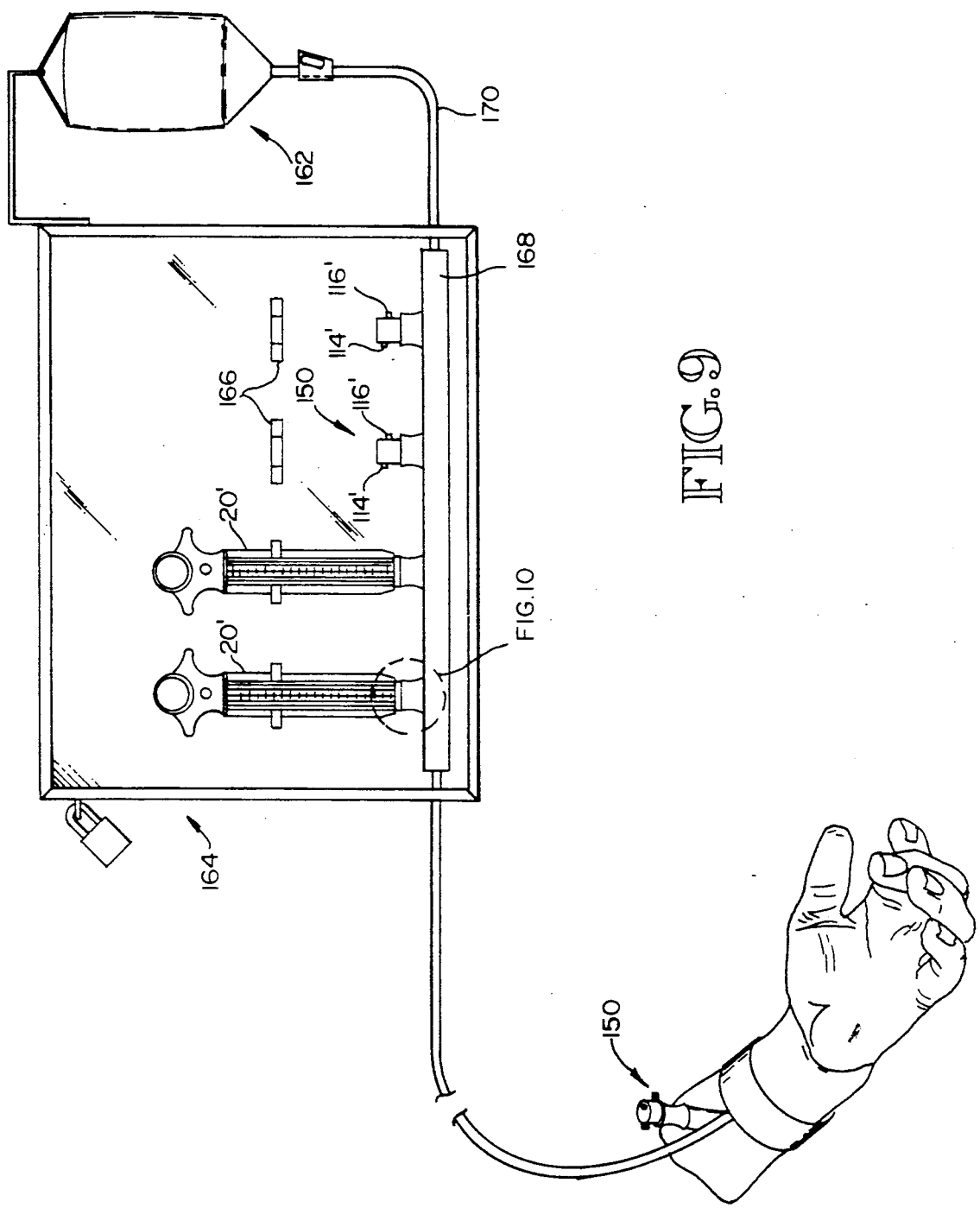
FIG. 9 is a diagrammatic representation of a plurality of multiple-dose reservoir syringes in use with a fluid-distribution manifold system.

FIG. 9 illustrates a multiple-dose fluid delivery system which provides a means for medicating a patient 160 with a plurality of different medicines, while virtually eliminating the introduction of bacteria or other undesirable contaminants into a conventional intravenous system 162. A securable storage case 164 has resilient clamps 166 for securing one or more multiple-dose reservoir syringes 20' thereto.

The storage case 164 also has a multiple-position manifold 168 in series with the intravenous line 170 of the intravenous system 162. The manifold 168 comprises a plurality of T-connectors, such as the T-connector 150 of FIG. 8, connected in series. However, an alternate embodiment of the multiple-dose reservoir syringe 20', shown in FIG. 10, is used. In this alternate embodiment, the lower end 34, of the inner cylinder 24 is modified so as to provide three positions of interaction between the external member 150' and the recessed cavity 88'. In this embodiment, the reduced diameter portion 112' is somewhat longer than the reduced diameter portion 112 of the embodiment shown in FIGS. 4, 5, and 8 so as to permit the upper and lower ears 114' and 116' to be inserted further into the recessed channel 88'.

In a first position, shown at reference numeral 112 in FIG. 10, the ears 114' and 116' engage a shelf 182, which axially aligns the multiple-dose fluid reservoir syringe 20' with the external member 150. However, in this first position, the aperture 110' is not engaged with the projection 110 on the rotating disk 86. Thus, the disk cannot be rotated into the fluid delivery position and fluid cannot be inadvertently ejected from the syringe.

By rotating the syringe 20, with respect to the external member 150' approximately 10 degrees, the reduced diameter portion 112' can be further inserted into the recessed cavity 88 to a second position 183, where the aperture 110' is engaged with the projection 94 on the rotating disk 86. In the second position, the rotating disk 86 is engaged, but fluid cannot be ejected from the inner cylinder 24.

Subsequent rotation of the syringe 20' to a third position 184 causes the disk 86 to be rotated into a fluid delivery position whereby depression of the plunger 22 will eject fluid into the manifold 186.

As best seen in FIG. 9, a complete course of medication for a patient can be provided inside the secured storage case 164. The health care professional need only rotate the appropriate syringe 20' from the first through third positions to inject a desired volume of any of the medicines available in the storage case into the patient. The syringe 20' can then be rotated into the first position to terminate fluid communication between that syringe and the manifold 168. In this manner, all of the necessary medicines for the patient can be stored at the patient's location, and all of the medicines are maintained in the sterile condition throughout the patient's treatment. Cross-contamination from one patient to another is eliminated because each patient is provided with his or her own set of syringes 20'.

Most medicines can be safely stored for long periods in the fluid reservoir 60 if the outer cylinder 33 is manufactured from polypropylene. However, certain highly reactive fluids may require the use of a glass liner in outer cylinder 33 to avoid an undesirable reaction of the fluid with the outer cylinder.

Other modifications and variations of the invention will be apparent to those of ordinary skill in the art. Thus, the invention is not to be limited by the above description, but is to be determined in scope by the claims which follow.

I claim:

1. A sterile, multiple-dose fluid delivery system, comprising:
   an inner cylinder having two ends, a fluid introduction channel, a fluid-ejection channel connected to the inner cylinder at one of the ends, and a reciprocating piston in the inner cylinder for accepting and ejecting a fluid charge;
   an outer, annular cylinder for storing the fluid in a sterile manner, the outer cylinder being coaxial with and rotatable about the inner cylinder between a first position in which the outer cylinder is in fluid communication with the fluid introduction channel and a second position in which the outer cylinder is not in communication with the fluid introduction channel, the outer cylinder also having vent means for permitting the introduction of air into the outer cylinder and for substantially preventing the introduction of undesirable bacteria into the outer cylinder; and
   a fluid-ejection valve connected to and selectively engageable with the fluid-ejection channel to selectively permit ejection of fluid from the inner cylinder wherein the fluid-ejection valve has a disk recessed so as to be protected from contamination and being rotatable between a fluid-permeable and a fluid-impermeable position with respect to the fluid-ejection channel so that fluid communication through the fluid-ejection channel is established by rotation of the disk, whereby multiple doses of fluid can be drawn into the inner cylinder and ejected therefrom without introducing contaminants into the cylinders.

2. The fluid delivery system of claim 1, including an external member having engagement means for engaging the disk.

3. The fluid delivery system of claim 2 wherein the external member has a hypodermic needle thereon.

4. The fluid delivery system of claim 2 wherein the external member is part of a fluid manifold having a plurality of such external members thereon and backflow prevention means in each external member to prevent reverse flow of fluid therethrough.

5. The fluid delivery system of claim 2 wherein the disk has a disk aperture therein for selective engagement with the fluid-ejection channel and wherein the disk also has a projection thereon for engagement by the engagement means.

6. The fluid delivery system of claim 5 wherein the inner cylinder and the engagement means define a two-position bayonet mechanism, wherein in a first position the external member and the disk are engaged but the disk aperture is misaligned with the fluid-ejection channel, and wherein in a second position the disk aperture and the fluid-ejection channel are aligned for passage of fluid therethrough.

7. The fluid delivery system of claim 6 wherein the bayonet mechanism has a third position in which the external member is at least partially retained by one of the cylinders but the disk is not engaged by the engagement means.

8. A first chamber having two ends and a reciprocating piston therein for accepting a fluid charge and a fluid-ejection channel connected to the first chamber at one of the ends for ejecting the fluid charge;
   a second chamber for storing the fluid in a sterile manner, the second chamber having vent means for permitting the introduction of air into the second chamber and for substantially preventing the introduction of undesirable bacteria into the second chamber;
   fluid communication means for selectively and fluidly communicating the first and second chambers with each other;
   a fluid-ejection valve connected to and selectively engageable with the fluid-ejection channel to selectively permit ejection of fluid from the first chamber wherein the fluid-ejection valve has a disk recessed so as to be protected from contamination and being rotatable between a fluid-permeable and a fluid-impermeable position with respect to the fluid-ejection channel so that fluid communication through the fluid-ejection channel is established by rotation of the disk, the disk also having a disk aperture therein for selective engagement with the fluid-ejection channel and a projection thereon for engagement by a disk engagement means including an external member having engagement means for engaging the disk, wherein at least one of the chambers and the disk engagement means define a three-position bayonet mechanism, wherein in a first position the external member and the disk are engaged but the disk aperture is misaligned with the fluid-ejection channel, wherein in a second position the disk aperture and the fluid-ejection channel are aligned for passage of fluid therethrough wherein in a third position the external member is at least partially retained by one of the chambers but the disk is not engaged by the engagement means and whereby multiple doses of fluid can be selectively drawn into the first chamber and ejected therefrom without introducing contaminants into the chambers.

* * * * *